United States Patent [19]

Rothfuss et al.

[11] Patent Number: 4,608,981
[45] Date of Patent: Sep. 2, 1986

[54] SURGICAL STAPLING INSTRUMENT WITH STAPLE HEIGHT ADJUSTING MECHANISM

[75] Inventors: Robert G. Rothfuss, Bellevue, Ky.; David K. Kuhl, Cincinnati, Ohio

[73] Assignee: Senmed, Inc., Cincinnati, Ohio

[21] Appl. No.: 662,908

[22] Filed: Oct. 19, 1984

[51] Int. Cl.$^4$ .............................................. A61B 17/11
[52] U.S. Cl. ................................ 128/305; 128/334 R; 227/19; 227/DIG. 1
[58] Field of Search ............. 128/334 R, 305; 227/19, 227/DIG. 1, 135, 152

[56] References Cited

U.S. PATENT DOCUMENTS

| | | | |
|---|---|---|---|
| D. 272,851 | 2/1984 | Green et al. | D24/26 |
| D. 272,852 | 2/1984 | Green et al. | D24/26 |
| 960,300 | 6/1910 | Fischer | 227/152 |
| 2,344,071 | 3/1944 | Wilson et al. | 227/19 |
| 3,017,637 | 1/1962 | Sampson | 227/19 X |
| 3,078,465 | 2/1963 | Bobrov | 128/334 R |
| 3,079,606 | 3/1963 | Bobrov | 217/76 |
| 3,315,863 | 4/1967 | O'Dea | 227/19 |
| 3,317,105 | 5/1967 | Astafjev et al. | 128/334 R X |
| 3,490,675 | 1/1970 | Green et al. | 227/19 |
| 3,499,591 | 3/1970 | Green | 227/76 |
| 3,551,987 | 1/1971 | Wilkinson | 128/334 R |
| 4,111,206 | 9/1978 | Vishnevsky et al. | 128/334 R X |
| 4,241,861 | 12/1980 | Fleischer | 227/135 |
| 4,244,372 | 1/1981 | Kapitanov et al. | 227/DIG. 1 X |
| 4,290,542 | 9/1981 | Fedotov et al. | 227/DIG. 1 X |
| 4,328,805 | 5/1982 | Akopov et al. | 128/334 R |
| 4,429,695 | 2/1984 | Green | 128/334 R X |
| 4,520,817 | 6/1985 | Green | 128/305 |

FOREIGN PATENT DOCUMENTS 1213583 3/1983 Australia .
599799 3/1978 U.S.S.R. ...................... 227/DIG. 1

Primary Examiner—Paul E. Shapiro
Attorney, Agent, or Firm—Charles P. Boukus, Jr.; Jerrold J. Litzinger

[57] ABSTRACT

A surgical stapling instrument suitable for performing a gastrointestinal anastomosis is provided. The stapling instrument incorporates a staple height adjusting mechanism which enables the gap between its jaw members to be adjusted to select different staple heights to be produced when the staples are formed. Preferably, the stapling instrument includes a pair of elongate jaw members, one of which supports a staple cartridge adapted to receive at least two laterally spaced longitudinal rows of staples, and the other provided with an anvil adapted to form the staples. A pusher bar and knife assembly slidable longitudinally relative to the jaw members sequentially drives the staples from the cartridge and forms the staples against the anvil to produce a pair of laterally spaced rows in the tissue. The pusher bar and knife assembly includes a knife blade for cutting the tissue along a line between the longitudinal staple rows. A set of jaw support members is carried by the knife blade which travel along the elongate jaw members as the pusher bar and knife assembly is advanced to provide local support to the jaw members. The angular orientation of the knife blade relative to the jaw members is adjustable by the staple height adjusting mechanism to vary the vertical spacing between the jaw support members as the gap between the jaw members is varied.

21 Claims, 16 Drawing Figures

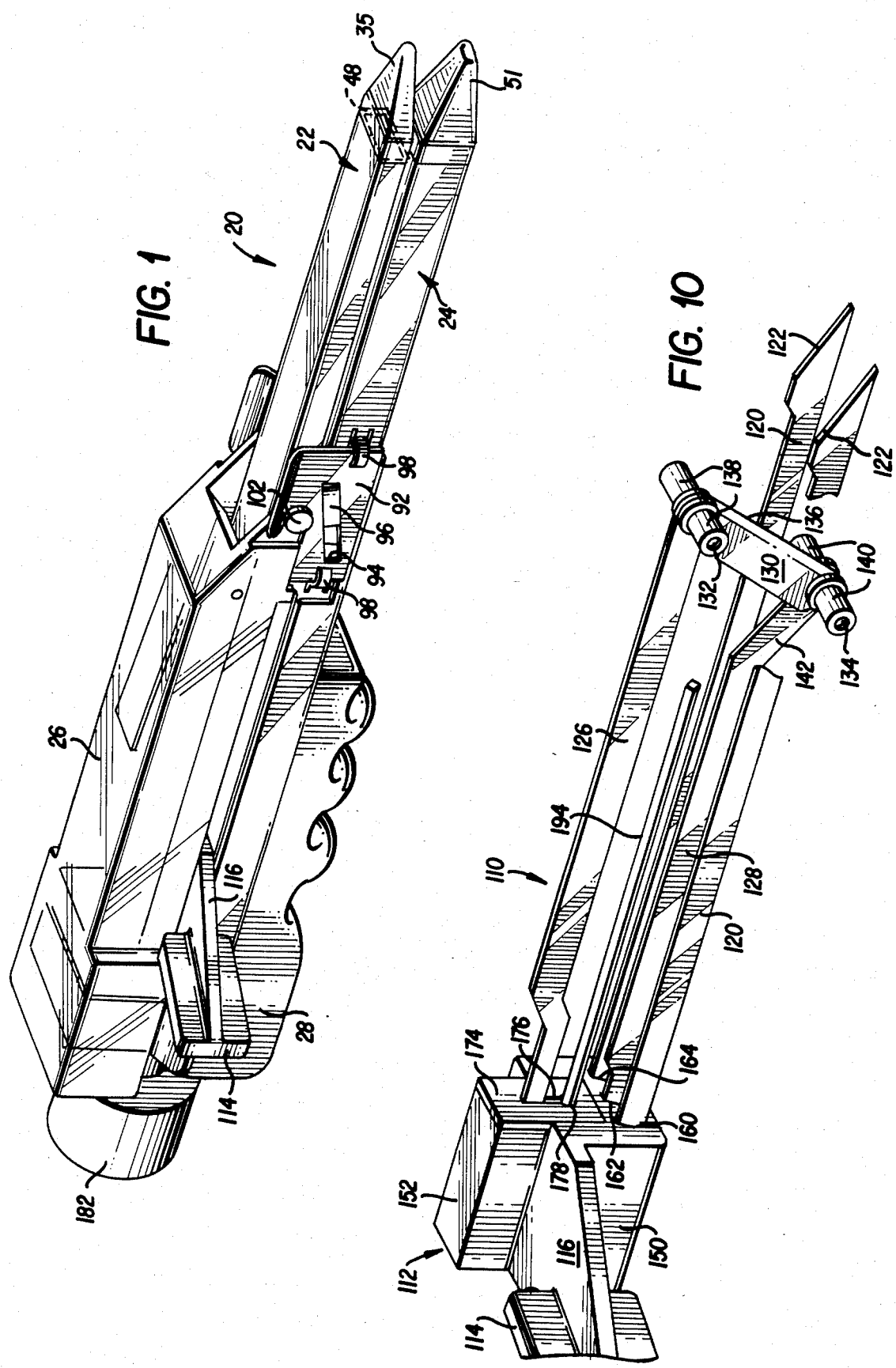

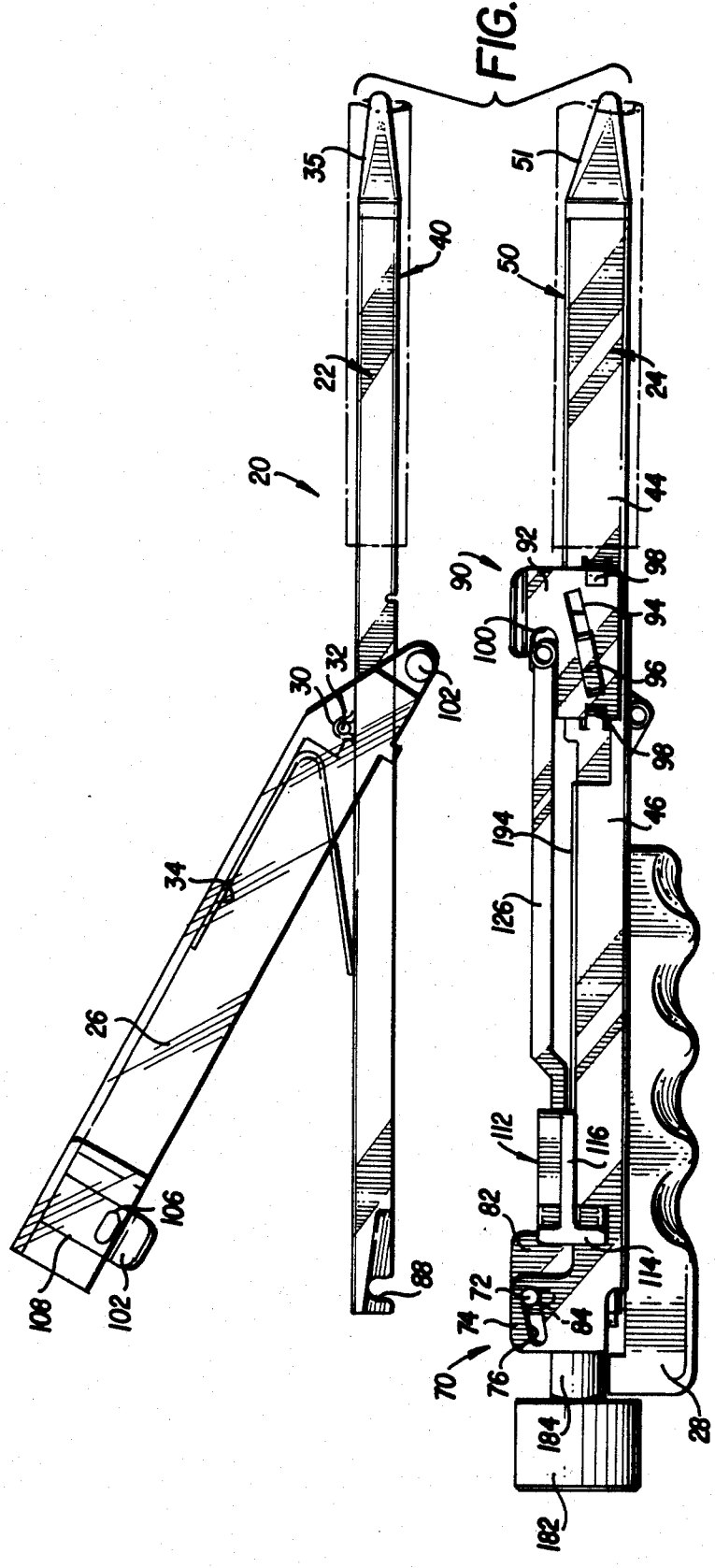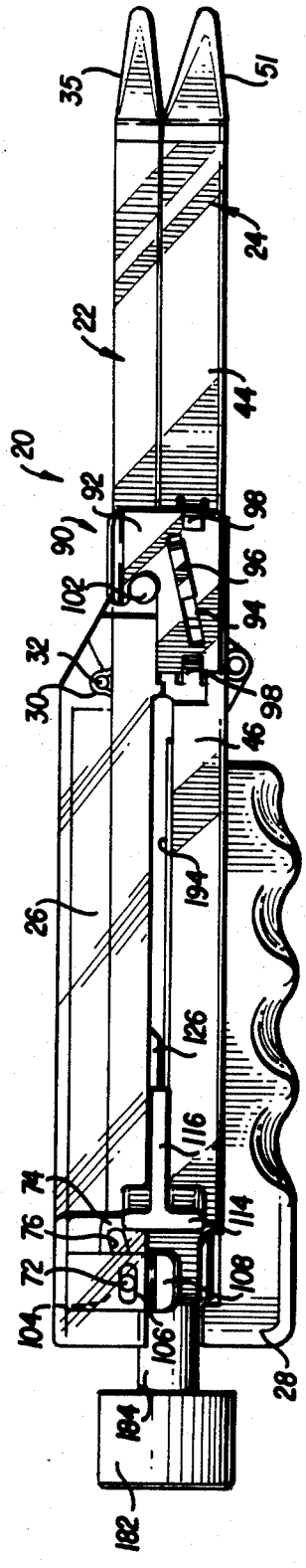

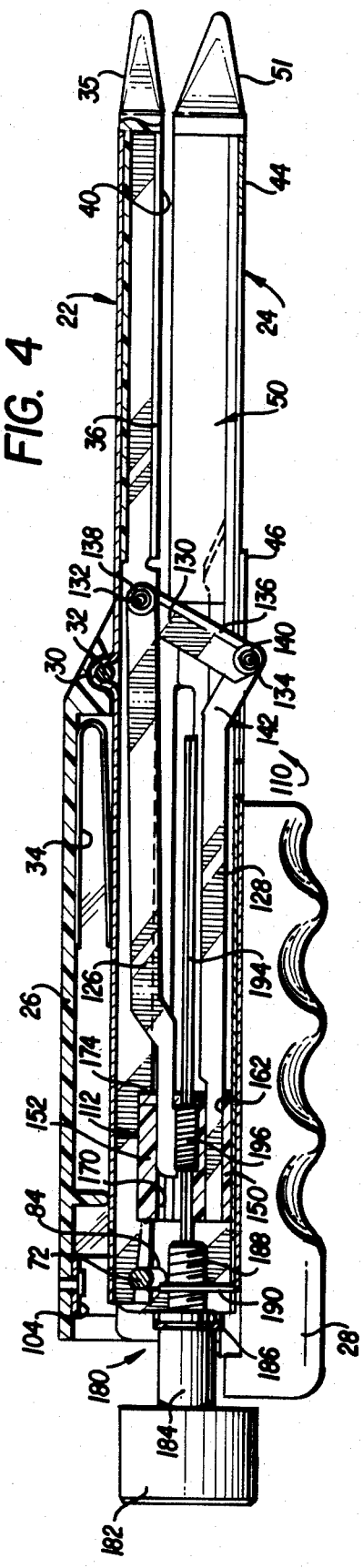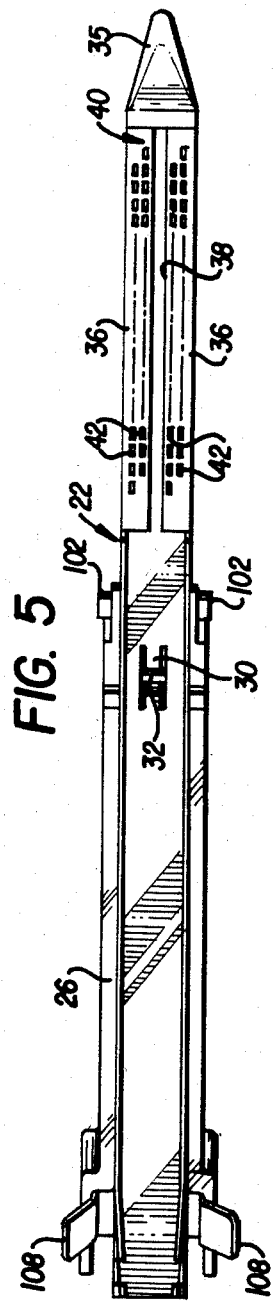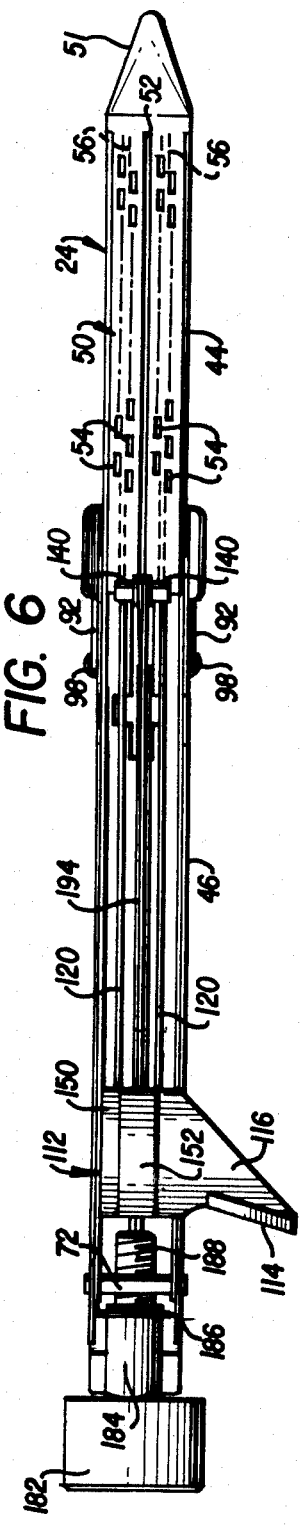

SURGICAL STAPLING INSTRUMENT WITH STAPLE HEIGHT ADJUSTING MECHANISM

FIELD OF INVENTION

The present invention relates to a surgical stapling instrument and, more particularly, to a gastrointestinal anastomotic stapling instrument for producing one or more rows of staples which advantageously enables different staple heights to be selected and produced by the same instrument. Specifically, this invention relates to a linear anastomotic stapling instrument including a staple height adjusting mechanism which enables the vertical gap between its elongate jaw members to be varied to select the different staple heights to be produced.

BACKGROUND AND PRIOR ART

In recent years, there has been an increasing tendency for surgeons to use stapling instruments to suture body organs and tissues such as lung, esophagus, stomach, duodenum and other body organs in the intestinal tract. The use of an appropriate stapling instrument in most instances performs a better job in less time and simplifies certain previously difficult surgical procedures such as gastrointestinal anastomoses.

In the prior art, the early linear two and four row cutting staplers were permanent instruments into which the staples were individually hand loaded. These staplers were very expensive, bulky, heavy and difficult to load and to clean for each surgical use. An example is disclosed in U.S. Pat. No. 3,315,105. An improvement of the permanent type surgical stapler was made by providing the basic stapling instrument with a presterilized disposable staple loading unit and with an optional knife for dividing the tissue simultaneously while forming the rows of staples. An example is disclosed in U.S. Pat. No. 3,499,591. However, this improvement mainly accomplished the saving of the time previously required to load the staples by hand. It was still necessary for the basic instrument to be disassembled, cleaned, reassembled and fitted with a new cartridge and anvil for each surgical procedure, in addition to the maintenance required of the stapling instrument itself. Another problem with this type of instrument is the tendency for the jaws to spread apart at the distal end after repeated use resulting in a substantial variation in the formed staple heights between the proximal and distal ends of the staple rows.

As hospital costs have continued to increase, it has become necessary to eliminate unnecessary work and develop more efficient techniques without compromise to the surgical procedure. Consequently, disposable stapling instruments of the type disclosed in U.S. Pat. No. 4,429,695 have been developed. In the disposable stapling instrument of this patent, an actuator and knife blade assembly provides local support to the stapler jaws in the region of the knife blade and pusher bar cams. However, this stapling instrument does not address the problem of accommodating tissue of different thicknesses. If the tissue is stapled too tightly, the blood supply is compromised and the tissue may necrose. If stapled too loosely, the tissue may hemorrhage, or in the case of hollow organs such as intestine, may also leak. Thus, both too tightly and too loosely formed staples can cause serious problems and complications.

Typically, a linear anastomotic stapling instrument includes a pair of cooperating elongate jaw members, each adapted to be inserted into internal, tubular body organs to be anastomosed. One of the jaw members supports a staple cartridge with at least two laterally spaced rows of staples, and the other jaw member supports an anvil with staple-forming pockets aligned with the rows of staples in the cartridge. Generally, a single pusher bar and knife assembly is slidable longitudinally along the jaw members to sequentially eject staples from the cartridge via camming surfaces which activate a plurality of staple drivers carried by the cartridge and associated with the individual staples to close the staples against the anvil and form laterally spaced rows of staples in the tissue gripped between the jaw members. A knife blade which trails the pusher bars cuts the tissue along a line between the staple rows. Examples of such anastomotic stapling instruments are disclosed in U.S. Pat. Nos. 3,499,591 and 4,429,695. In neither instance is any provision made for selection of different staple heights to be produced by the same instrument.

In the use of stapling instruments of the above type, relatively large forces are exerted in clamping the tissue to be fastened between the jaw members, ejecting the staples from the staple cartridge, driving the staples into the gripped tissue, and forming the staples against the anvil. Such forces tend to separate the jaw members vertically and to distort the jaw members laterally, with the result that the consistency of the formed staple height is diminished, or that the staples may sometimes miss the anvil completely. This problem is accentuated in the case of a disposable stapling instrument in which relatively lightweight disposable materials are used for the manufacture of the jaw members and other components. Thus, there is a need for a disposable stapling instrument which is capable of accurate alignment of the jaw members while the staple forming operation is performed, and which provides adequate support for its elongate jaw members to withstand the large forces encountered in the operation of the stapling instrument.

In the past, surgical stapling instruments have been designed to produce only one predetermined staple height. Thus, to enable a surgeon to select different staple heights, e.g., to accommodate tissue of different thicknesses, separate stapling instruments each loaded with different staple sizes have been necessary for instances where different staple heights are required. Accordingly, it is highly desirable to provide a stapling instrument which is adjustable for selection of different staple heights to allow the stapling instrument to be used with tissue of different thicknesses.

SUMMARY OF INVENTION

The present invention achieves an improved surgical stapling instrument which overcomes the disadvantages of the prior art by incorporating a staple height adjusting mechanism which enables different staple heights to be selected and produced by the same instrument. Preferably, the adjusting mechanism operates by varying the gap or vertical spacing between the jaw members to select the different staple heights to be produced. In addition, the stapling instrument is adapted to maintain the jaw members in a spaced and aligned parallel relationship as the gap or vertical spacing therebetween is varied.

The present invention is embodied in a linear gastrointestinal stapling instrument provided with elongated jaw members for gripping tissue therebetween. A staple cartridge carrying at least two laterally spaced longitudinal rows of staples is mounted on one of the jaw members, and a staple forming anvil is provided on the other jaw member. A pusher bar and knife blade assembly is slidably mounted for longitudinal movement relative to the jaw members. The pusher bar and knife blade assembly includes cam means for driving the staples from the staple cartridge into tissue gripped between the jaw members and forming the staples against the anvil to form a pair of laterally spaced staple rows in the tissue, and knife means for cutting the tissue gripped between the jaw members along a line between the staple rows. The stapling instrument includes adjusting means for varying the gap or vertical spacing between the elongate jaw members to select different staple heights to be produced when the staples are formed.

Preferably, the pusher bar and knife blade assembly includes a pair of jaw support members each cooperable with one of the elongate jaw members as the assembly is advanced to provide local support to the elongate jaw members, and means for adjusting the vertical spacing of the jaw support members as the vertical spacing between the elongate jaw members is varied. Preferably, the assembly includes a knife blade oriented at an angle relative to the elongate jaw members with the jaw support members being carried by the knife blade assembly. The knife blade is adjustable to vary its angle of orientation relative to the elongate jaw members and to vary the vertical spacing between its jaw support members.

A preferred embodiment of the linear anastomotic stapling instrument includes upper and lower cooperating elongate jaw members, one of which includes a staple cartridge adapted to receive at least two laterally spaced longitudinal rows of staples and provided with staple drivers for driving the staples from the cartridge, and the other including an anvil adapted to form the staples. A pusher block is slidably mounted for longitudinal movement along one of the jaw members and provided with a pair of staple pusher bars including cam surfaces engageable with the staple drivers for sequentially driving the staples from the cartridge and forming the staples against the anvil to produce at least a pair of laterally spaced staple rows in the tissue. A knife blade is adjustably connected to the pusher block and provided with a cutting edge oriented at an angle relative to the elongate jaw members. First and second jaw support means are mounted on the knife blade for engaging the elongate jaw members as the pusher block is advanced to provide local support to the jaw members. An adjusting mechanism is provided for varying the vertical spacing between the jaw members and for adjusting the angular orientation of the knife blade to vary the vertical spacing of the jaw support means to select different staple heights to be produced when the staples are formed.

The preferred embodiment of the linear anastomotic stapling instrument includes support means adapted to maintain the jaw members in a spaced, parallel arrangement as the vertical spacing between the jaw members is varied. Preferably, the support means includes a rear pivot connection for pivotally connecting the rearward ends of the elongate jaw members together, and a pair of gap setting plates for connecting the elongate jaw members together at any intermediate position. The rear pivot connection is adjustable vertically to vary the spacing between the rearward ends of the jaw members, and the gap setting plates are adjustable vertically to vary the spacing between the anvil and staple cartridge carried by the jaw members. The adjusting mechanism is adapted to simultaneously adjust the rear pivot connection and the gap setting plates to maintain the jaw members in a spaced, parallel relationship as the vertical spacing therebetween is varied.

Preferably, the staple cartridge carrying jaw member comprises an elongated channel-shaped frame provided with a slidable, telescoping section slidably mounted for longitudinal movement relative to the channel-shaped frame. The slidable section is operatively coupled to the rear pivot connection, to the gap setting plates, and to the adjusting mechanism. The adjusting mechanism is adapted to displace the slidable section longitudinally relative to the channel-shaped frame of the staple cartridge carrying jaw member to adjust the height of the rear pivot connection and the gap setting plates to vary the vertical spacing between the jaw members.

In the preferred embodiment, the knife blade is vertically oriented and pivotally connected at first and second pivot points to a pair of support bars which extend longitudinally from the pusher block. The adjusting mechanism includes means for displacing one of the knife support bars longitudinally relative to the other knife support bar to vary the angular orientation of the knife blade and to adjust the vertical spacing of the jaw support means carried by the knife blade in accordance with the vertical spacing between the elongate members. Preferably, a screw or cam member is rotatably mounted on the pusher block with one of the knife support bars being engageable with the screw member to permit the knife support bar to be advanced or retracted relative to the pusher block upon rotation of the screw member to adjust the angular orientation of the knife blade. An adjusting knob is rotatably mounted at the rearward end of one of the elongate jaw members with an adjusting rod extending axially from the adjusting knob and mounted for rotation therewith. The adjusting rod is slidably connected and keyed to the screw member to transmit rotation of the adjusting knob to the screw member and to permit the pusher block and screw member to be advanced axially relative to the adjusting knob.

In the preferred embodiment of the linear anastomotic stapling instrument, the anvil carrying jaw member includes an elongated passageway located above the anvil for receiving the first jaw support means as the pusher block is advanced to allow the first jaw support means to travel along the anvil and provide local support to the anvil carrying jaw member. The staple cartridge carrying jaw member includes an elongated slot through which a portion of the knife blade protrudes. The second jaw support means is mounted on the protruding portion of the knife blade and located beneath the cartridge carrying jaw member to allow the second jaw support means to travel along and provide local support to the jaw member. Preferably, each jaw support means comprises one or more rollers mounted at each of the first and second pivot points which connect the knife support bars to the knife blade.

The invention provides an improved linear gastrointestinal anastomotic stapling instrument which advantageously allows different staple heights to be selected and produced by the same stapling instrument. In addition, the stapling instrument achieves accurate and precise rows of staples because the pusher bar and knife blade assembly provides local support along the jaw members during the stapling and cutting action performed by the instrument.

BRIEF DESCRIPTION OF DRAWINGS

FIG. 1 is an overall perspective view of a linear anastomotic stapling instrument embodying the principles of the present invention;

FIG. 2 is a side elevation showing the anastomotic stapling instrument partially disassembled;

FIG. 3 is a side elevation showing the anastomotic stapling instrument in its assembled configuration;

FIG. 4 is a side elevation, partially in section, of the anastomotic stapling instrument;

FIG. 5 is a bottom view of the anvil carrying jaw member of the anastomotic stapling instrument;

FIG. 6 is a top view of the staple cartridge carrying jaw member of the anastomotic stapling instrument;

FIG. 10 is an enlarged perspective view of a pusher bar and knife blade assembly of the anastomotic stapling instrument;

DETAILED DESCRIPTION OF PREFERRED EMBODIMENT

Figure 7:
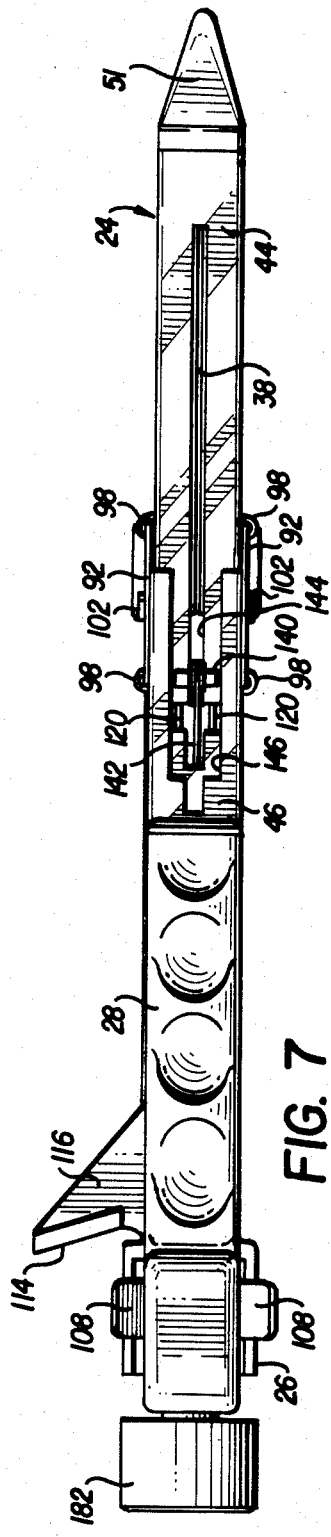
FIG. 7 is a bottom view of the staple cartridge carrying jaw member of the anastomotic stapling instrument.

Referring to FIGS. 1 and 2, the present invention is embodied in a linear anastomotic stapling instrument, generally 20, comprising an upper elongated anvil carrying jaw member 22 and a lower elongated staple cartridge carrying jaw member 24. Upper anvil carrying jaw member 22 is provided with a handle 26 pivotally connected to the jaw member. Lower staple cartridge carrying jaw member 24 is provided with a handle 28 suitably shaped to form a hand grip which facilitates the handling and operation of the stapling instrument by a surgeon. Preferably, handles 26 and 28 are made of plastic or other lightweight material, while jaw members 22 and 24 are made of stainless steel or a similar material.

As shown in FIGS. 1 and 2, upper jaw member 22 comprises a one-piece elongated channel-shaped frame. At an intermediate position along the top surface of upper jaw member 22, an upstanding ear 30 is formed which receives a transverse pivot pin 32 mounted in suitable openings formed in the side walls of handle 26 to pivotally connect the handle to the upper jaw member. An elongated leaf spring 34 (FIG. 2) attached to pivot handle 26 engages the top surface of upper jaw member 22 and urges the rearward end of the handle to an upwardly inclined position relative to the jaw member. A tapered tip 35 is mounted at the front of upper jaw member 22 to facilitate the insertion of the jaw member into hollow, tubular body organs.

Figure 8:
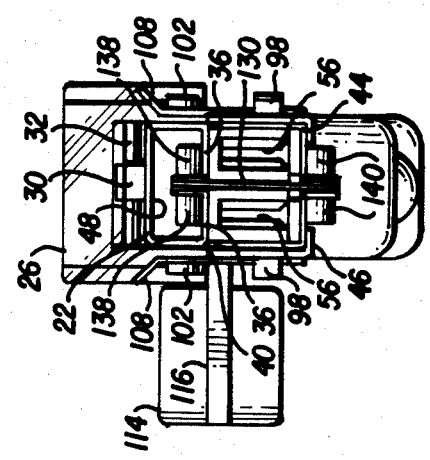
FIG. 8 is a front end view of the anastomotic stapling instrument with its tapered tips removed.

Referring to FIG. 5, the front portion of upper jaw member 22 is provided with a pair of elongated, inwardly extending flanges 36, separated by a central longitudinal slot 38, which define an anvil 40 of the stapling instrument. Each flange 36 is provided with two longitudinal rows of uniformly spaced staple-forming pockets 42. As shown in FIG. 8, flanges 36 together with the interior walls of upper jaw member 22 define a longitudinal passageway 48 located above anvil 40.

Referring to FIGS. 6 and 7 lower cartridge carrying jaw member 24 comprises an assembly including an elongated, channel-shaped frame 44 and another channel-shaped frame section 46 which are slidably connected for longitudinal movement relative to each other. Channel-shaped frame 44 of lower jaw member 24 is substantially the same in length as the other channel-shaped frame which forms upper jaw member 22. As shown in FIG. 8, channel-shaped frame section 46 is slightly larger in cross-section than channel-shaped frame 44 of lower jaw member 24. Thus, frame section 46 is slidable longitudinally relative to elongated frame 44 for purposes explained in more detail below.

As shown in FIG. 6, lower jaw member 24 supports a staple cartridge 50 which is adapted to receive a plurality of surgical staples arranged in at least two laterally spaced longitudinal rows. Staple cartridge 50 is mounted at the front portion of channel-shaped frame 44 and is divided longitudinally by a central, elongated slot 52 which extends from the proximal end of the cartridge to its distal end. The front or distal end of staple cartridge 50 includes a tapered tip 51 to facilitate the insertion of lower jaw member into a hollow, tubular body organ.

Preferably, a plurality of staple openings 54 formed in staple cartridge 50 are arranged in two pairs of laterally spaced rows, with each pair of rows being disposed on opposite sides of central longitudinal slot 52. A plurality of surgical staples 55 (FIG. 16) are mounted within the openings 54 of the cartridge. As shown in FIG. 6, the staple openings 54 in adjacent rows are staggered to provide more effective stapling of the tissue when the instrument is operated. Staple cartridge 50 also includes a pair of longitudinal slots 56 located on opposite sides of elongated central slot 52 and disposed between the staggered rows of openings 54 on each side of central slot 52. Each longitudinal slot 56 extends from the proximal end of cartridge 50 to its distal end.

Figure 16:
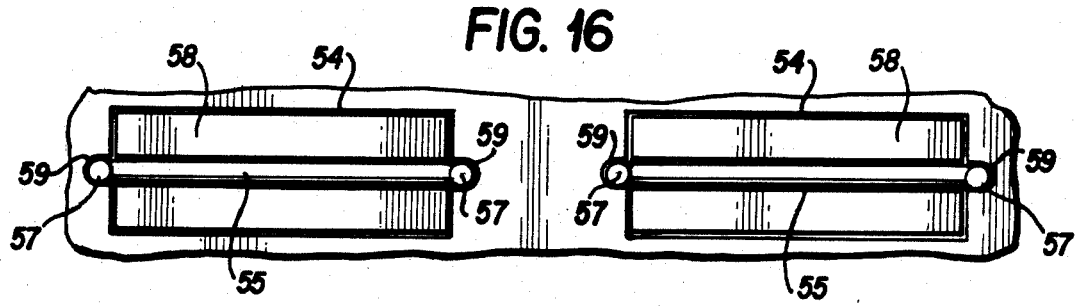
FIG. 16 is an enlarged top view of a portion of the staple cartridge of the anastomotic stapling instrument.

As shown in FIG. 16, a plurality of staple drivers 58 is slidably mounted in staple openings 54 for actuating staples 55 which are loaded into the cartridge. Preferably, each staple driver 58 is designed to simultaneously actuate two staples located in adjacent rows. Thus, a first set of staple drivers 58 (FIG. 13) is provided for actuating the staples in a pair of staggered rows located on the side of central longitudinal slot 52 (FIG. 6), and a second set of staple drivers (not shown) is provided for actuating the staples in a pair of staggered rows located on the other side of central longitudinal slot 52. Each staple receiving opening 54 of cartridge 50 is provided with a pair of vertical grooves 59 (FIG. 16) at its opposite ends for receiving and guiding the staple legs 57 as the staples 55 are driven from the cartridge.

In accordance with the invention, the anvil carrying jaw member 22 and the staple cartridge carrying jaw member 24 are mounted for relative vertical movement to permit adjustment of the gap between staple cartridge 50 and anvil 40 to select different staple heights to be produced. Preferably, as shown in FIGS. 2 and 3, the stapling instrument 20 is provided with support means comprising a rear pivot connection, generally 70, and a gap setting mechanism, generally 90, which are adjustable to vary the vertical spacing between jaw members 22 and 24. Adjustable pivot connection 70 and gap setting mechanism 90 are also adapted to maintain upper and lower jaw members 22 and 24 in a spaced, parallel relationship as the vertical spacing between the jaw members is varied. In addition, the rear pivot connection 70 and the gap setting mechanism 90 slidably connect elongated, channel-shaped frame 44 to frame section 46 of lower jaw member 24 for relative longitudinal movement.

Referring to FIG. 2, rear pivot connection 70 includes a transverse pivot pin 72 extending between a pair of upstanding arms 74 formed at opposite sides at the rear of channel-shaped frame section 46. Each arm 74 includes an inclined pivot pin slot 76 for slidably receiving the opposite ends of pivot pin 72. Preferably, each slot 76 is sloped upwardly at the same angle, e.g. between 5° and 30°. Similarly, a pair of upstanding arms 82 is provided at opposite sides at the rear of channel-shaped frame 44. Each arm 82 is provided with a vertical pivot pin slot 84 in which pivot pin 72 is slidably received. A pair of notches 88 is provided at opposite sides of upper channel-shaped jaw member 22 for receiving pivot pin 72 to pivotally connect the upper and lower jaw members. As shown in FIG. 2, rear pivot connection 70 permits upper jaw member 22 to be detached from lower jaw member 24 to facilitate use of the stapling instrument in certain surgical procedures.

Referring to FIGS. 2 and 6, gap setting mechanism 90 includes a pair of jaw support plates 92 which are adjustably mounted at an intermediate position along opposite sides of lower jaw member 24. Each support plate includes an elongated rectangular slot 94 with its forward end sloped upwardly relative to the elongate jaw members. Preferably, slots 94 are sloped upwardly at the same angle, e.g., between 5° and 30°, as slots 76 of the rear pivot connection 70. A pair of raised, outwardly projecting lugs 96 formed on opposite sides of slidable frame section 46 are slidably disposed in the corresponding slots 94 of jaw support plates 92. Each lug 96 is rectangular in configuration with its forward end inclined upwardly at the same angle as the corresponding slot 94. In addition, a pair of side supports 98 (FIGS. 3 and 7) is located on each side of the lower channel-shaped frame 44 which extend over the opposite vertical edges of each support plate 92. The side supports 98 permit the jaw support plates 92 to move at a right angle relative to the lower channel-shaped frame 44 as raised lugs 96 slide along slots 94 in the support plates to adjust the gap between the upper and lower jaw members 22 and 24.

As shown in FIG. 2, the upper portion of each support plate 92 is provided with a rearwardly facing slot 100 for receiving a raised, cylindrical lug 102 which projects outwardly from each side wall of handle 26. With upper and lower jaw members 22 and 24 pivotally connected at rear pivot connection 70 by inserting pivot pin 72 on the lower jaw member into slots 88 provided on the upper jaw member, the jaw members can be pivoted together to align cylindrical lugs 102 on handle 26 with rearwardly facing slots 100 of support plates 92. Thereafter, as handle 26 is pivoted downwardly toward the rear portion of upper jaw member 22, cylindrical lugs 102 are moved into slots 100 of the support plates. At the same time, a U-shaped latching spring 104 provided at the rear end of handle 26 engages pivot pin 72 to latch the handle in a closed position. A pair of slots 106 are provided on opposite sides 108 of latching spring member 104 to receive the opposite ends of pivot pin 72 which project outwardly from slots 76 formed in upstanding arms 74 of slidable frame section 46. To unlatch handle 26, the opposite sides 108 of spring 104 can be manually shifted outwardly to disengage pivot pin 72 from slots 106.

Referring to FIGS. 4 and 10, the preferred embodiment of the stapling instrument includes an improved pusher bar and knife blade assembly, generally 110, which is slidably mounted for longitudinal movement relative to upper and lower jaw members 22 and 24, respectively, for driving the staples from staple cartridge 50 into tissue gripped between the jaw members, shaping the staples against anvil 40, and cutting the tissue along a line between the rows of staples formed in the tissue. The pusher bar and knife blade assembly includes a pusher block 112 (FIG. 6) which is slidably received within the lower channel-shaped frame 44. Pusher block 112 includes a laterally positioned actuator 114 connected to the pusher block by a tapered flange 116 extending laterally through the space between the upper and lower jaw members.

Figure 13:
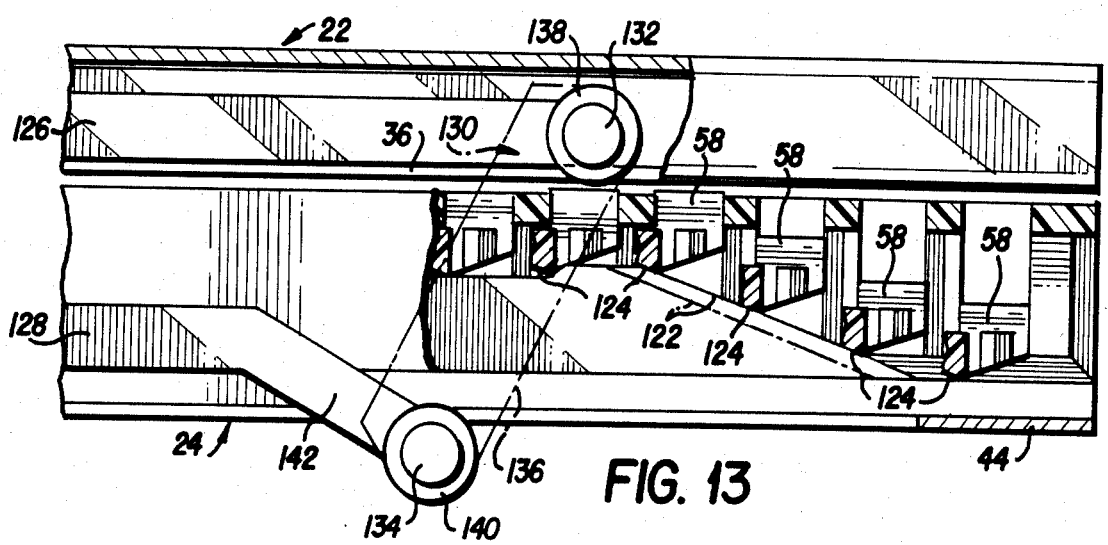
FIG. 13 is an enlarged, partially cutaway view of the anvil and staple cartridge carrying jaw members, illustrating the operation of the pusher bar and knife assembly.

The pusher bar and knife blade assembly 110 includes a pair of elongated staple pusher bars 120 (FIG. 6) projecting forwardly from pusher block 112 and slidably received in elongated slots 56 of staple cartridge 50. As shown in FIGS. 4 and 10, the front end of each staple pusher bar 120 is provided with a wedge-shaped tip which defines an inclined cam surface 122 for engaging staple drivers 58 as the pusher bars are advanced into staple cartridge 50. Preferably, the wedge-shaped tips of staple pusher bars 120 are offset longitudinally with one cam surface 122 located slightly ahead of the other cam surface. As shown in FIG. 13, each staple driver 58 is provided with a sloped surface 124 oriented at the same angle as cam surface 122 of each staple pusher bar 120 to provide a flat, sliding contact between these surfaces.

Referring to FIGS. 4 and 10, the pusher bar and knife blade assembly 110 includes a pair of knife support bars 126 and 128 connected to a knife blade 130 by pivot shafts 132 and 134, respectively. Knife blade 130 includes a beveled cutting edge 136 which is oriented at an angle relative to elongate jaw members 22 and 24 and which is slidably received in central longitudinal slot 52 of staple cartridge 50.

In the preferred embodiment of the stapling instrument, upper and lower jaw support members are mounted on the pusher bar and knife blade assembly to provide local support for the elongate jaw members as the assembly is advanced. Preferably, upper pivot shaft 132 is provided with a pair of cylindrical rollers 138 mounted at its opposite ends which facilitate movement of the upper pivot shaft into the longitudinal passageway 48 above anvil flanges 36. As upper pivot shaft 132 is moved into the longitudinal passageway, rollers 138 travel along the top surfaces of anvil flanges 36 to provide local support for upper jaw member 22 during the stapling and cutting action performed by the instrument. Similarly, lower pivot shaft 134 is provided with a pair of cylindrical rollers 140 mounted at its opposite ends. Knife support bar 128 is bent downward at its front end 142 and extends through a central longitudinal slot 144 (FIG. 7) provided in the bottom surface of lower channel-shaped frame 44 and through a slot 146 formed in the bottom surface of slidable frame section 46. As a result, lower pivot shaft 134 is located beneath jaw member 24 and rollers 140 travel along the bottom surface of the jaw member as knife blade 130 is advanced to provide local support to the lower jaw member during the stapling and cutting action of the instrument. Preferably, as explained in more detail below, the angle of orientation of knife blade 130 relative to the upper and lower jaw members is adjustable to vary the vertical spacing between rollers 138 and 140 on pivot shafts 132 and 134 as the gap between the jaw members is adjusted.

Figure 11:
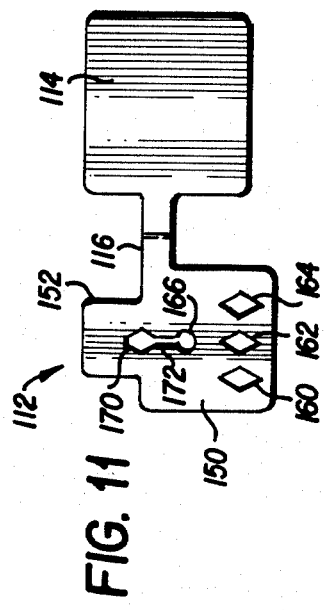
FIG. 11 is a rear view of a pusher block which is a component of the pusher bar and knife blade assembly of the anastomotic stapling instrument.
Figure 12:
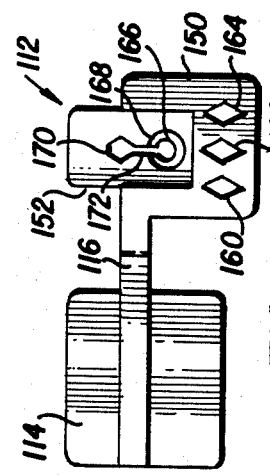
FIG. 12 is a front view of a pusher block which is a component of the pusher bar and knife blade assembly of the anastomotic stapling instrument.

Referring to FIG. 10, pusher block 112 includes a lower, rectangular body 150 provided with an upper rectangular section 152 which is reduced in width. As shown in FIGS. 4 and 6, rectangular body 150 is slidably disposed within elongated channel-shaped frame 44 of lower jaw member 24. With handle 26 latched in place (FIG. 3), upper rectangular section 152 of pusher block 112 is received between the opposite sides of the channel-shaped frame which forms upper jaw member 22. As shown in FIGS. 11 and 12, tapered flange 116 extends outwardly from one side of rectangular body 150 and supports actuator 114 for sliding pusher block 112 along the jaw members.

Referring to FIGS. 11 and 12, a set of three equidistantly spaced passages 160, 162 and 164 extend longitudinally through lower rectangular body 150 of pusher block 112. As shown in FIG. 10, the rear ends of staple pusher bars 120 are inserted into passages 160 and 164 to fix the pusher bars to pusher block 112. The rear end of lower knife support bar 128 is inserted into passage 162 to fix the knife support bar to pusher block 112.

As shown in FIG. 11, lower rectangular body 150 of pusher block 112 is provided with a circular bore 166 which extends forwardly from the rear face of rectangular body 150. A counterbore 168 (FIG. 12) extends rearwardly from the front face of pusher block 112 in axial alignment with circular bore 166. An upper passage 170 extends longitudinally through upper rectangular section 152 of the pusher block. Upper passage 170 is connected to circular bore 166 and counterbore 168 by a vertical slot 172 which extends longitudinally through pusher block 112 from its front face to its rear face. As shown in FIG. 4, the rear end of upper knife support bar 126 is slidably received within upper passage 170 of pusher block 112. A rectangular cover plate 174 is mounted on the front face of pusher block 112. Cover plate 174 includes a vertical slot 176 (FIG. 10) which receives the rear end of upper knife support bar 126. A circular bore 178 is provided in cover plate 174 at the bottom of vertical slot 176 in axial alignment with cylindrical bore 166 (FIG. 11) and counterbore 168 (FIG. 12) of pusher block 112.

In accordance with the invention, the stapling instrument is provided with means for selecting different staple heights to be produced when the staples are formed. In the preferred embodiment, this means is embodied as an improved adjusting mechanism for varying the vertical spacing between the jaw members to enable different staple heights to be selected. The adjusting means is also operative to adjust the angular orientation of the knife blade relative to the jaw members to vary the vertical spacing between the jaw support members carried by the knife blade.

In the preferred embodiment of the stapling instrument, an adjusting mechanism, generally 180, includes a cylindrical adjusting knob 182 rotatably mounted at the rearward end of lower channel-shaped frame 44. As shown in FIGS. 4 and 6, adjusting knob 182 includes a first, reduced diameter cylindrical section 184 which abuts a rear flange 186 extending perpendicularly inward from one side of frame 44 and a second, externally threaded cylindrical portion 188 of smaller diameter which extends forwardly from cylindrical section 184 and is rotatably mounted in a circular opening provided in flange 186. The externally threaded portion 188 of adjusting knob 182 is threadably received in a circular opening provided in an upstanding flange 190 formed at the rear of slidable frame section 46. Upon rotation of adjusting knob 182, flange 190 is displaced longitudinally relative to flange 186 to move slidable jaw section 46 relative to channel-shaped frame 44. As a result, adjustable pivot connection 70 and gap setting mechanism 90 are adjusted to vary the vertical spacing between upper and lower jaw members 22 and 24.

In addition, an elongated adjusting rod 194 which is square in cross section extends forwardly from reduced diameter portion 188 of adjusting knob 182 into central bore 166 (FIG. 11) provided in the rear face of pusher block 112 and outward from circular opening 178 (FIG. 10) formed in cover plate 174 on the front face of the pusher block. A set screw 196 (FIG. 4) comprising an externally threaded sleeve is rotatably mounted within counterbore 168 (FIG. 12) of pusher block 112. As shown in FIG. 4, set screw 196 is confined within the interior of pusher block 112 by cover plate 174. Preferably, set screw 196 is slidable along adjusting rod 194 and keyed for rotation with the adjusting rod. In the preferred embodiment, adjusting rod 194 has a non-circular, e.g., square cross-section and set screw 196 includes an axial passage of a similar configuration. As a result, set screw 196 is slidably mounted on adjusting rod 194 and rotatable therewith in response to rotation of adjusting knob 182.

As shown in FIG. 4, the rear end of upper knife support bar 126 has a lower serrated edge for engagement with the external threads of set screw 196. Upon rotation of set screw 196 via adjusting knob 182 and rod 194, the rear end of upper knife support bar 126 is retracted or advanced relative to pusher block 112 to pivot knife blade 130 about lower pivot shaft 134 to adjust its angle of orientation relative to upper and lower jaw members 22 and 24. As a result, the vertical spacing between jaw support rollers 138 and 140 on pivot shafts 132 and 134 is varied in accordance with the gap selected between the jaw members.

Figure 9:
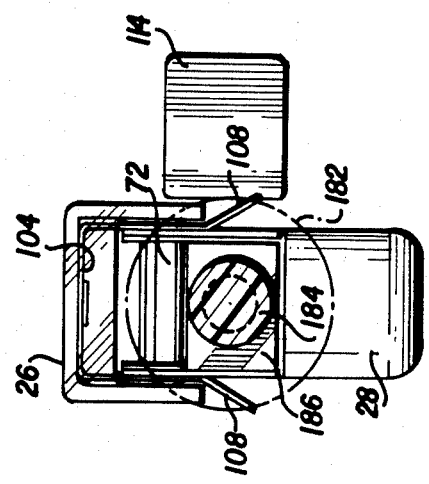
FIG. 9 is a rear end view, partially cutaway, of the anastomotic stapling instrument.

As shown in FIG. 3, when slidable frame section 46 is located in its forwardmost position relative to lower elongated frame 44, pivot pin 72 and support plates 92 are moved to the lowermost positions to define the minimum gap between jaw members 22 and 24 and select the smallest staple height. When adjusting knob 182 is rotated counter-clockwise, as viewed in FIG. 9, flange 190 (FIG. 4) is moved rearwardly towards flange 186 to slide frame section 46 rearwardly relative to channel-shaped frame 44. As slidable frame section 46 is retracted, inclined slots 76 formed in rear upstanding arms 74 translate the longitudinal movement of frame section 46 into upward vertical movement of pivot pin 72 within slots 84 formed in the upstanding arms 82 of channel-shaped frame 44. Thus, as pivot pin 72 is raised relative to channel-shaped frame 44, the rear end of upper jaw member 22 is displaced upwardly relative to lower jaw member 24.

Simultaneously, the longitudinal movement of frame section 46 is translated by inclined slots 94 and raised lugs 96 into upward vertical movement of support plates 92. The support plates are moved upwardly by substantially the same distance as rear pivot pin 72. Consequently, the spaced, parallel relationship of jaw members 22 and 24 is maintained. With jaw section 46 completely retracted, pivot pin 72 is moved to its uppermost position in vertical slots 84 and lugs 96 are moved to the lowermost position in slots 94 to raise support plates 92 to the uppermost position. Thus, as shown in FIG. 4, the maximum gap is established between the jaw members to select the largest staple height.

In the operation of stapling instrument 20, the tissue to be stapled and cut must be initially placed between jaw members 22 and 24 and clamped by the jaw members. Thus, handle 26 is unlatched by disengaging opposite sides 108 of its latching spring 104 from pivot pin 72 to allow the handle to pivot upwardly under the action of leaf spring 34. As a result, cylindrical lugs 102 on handle 26 are disengaged from slots 100 formed in support plates 92. Thereafter, upper and lower jaw members 22 and 24 can be separated by disengaging pivot pin 72 from slots 88 formed in the upper jaw member.

Next, the tissue to be stapled and cut is placed on jaw members 22 and 24. For example, as shown in FIG. 2, a piece of tubular, intestinal tissue may be slipped onto the front portion of each jaw member. After the tissue is placed on the jaw members, the stapling instrument is reassembled. The reassembly can be accomplished by aligning rear pivot pin 72 with slots 88 of anvil carrying jaw member 22, or by aligning cylindrical lugs 102 on handle 26 with slots 100 formed in support plate 92. Thereafter, handle 26 is pivoted downward until slots 106 of latching spring 104 engage pivot pin 72 to latch the jaw members together and to clamp the tissue therebetween.

The desired staple height can be selected either immediately after the tissue is placed on the jaw members and prior to reassembly of the stapling instrument, or immediately after the stapling instrument is reassembled and the tissue gripped between the jaw members. To select the desired staple height, adjusting knob 182 is rotated to move slidable frame section 46 relative to lower channel-shaped frame 44. As a result, simultaneous vertical movement is imparted to rear pivot pin 72 and intermediate support plates 92 to vary the gap between jaw members 22 and 24. The simultaneous vertical movement of pivot pin 72 and support plate 92 insures that the jaw members remain in a spaced, parallel arrangement as the gap between the jaw members is adjusted.

At the same time, the angular orientation of knife blade 130 is adjusted to vary the vertical spacing between cylindrical jaw support members 138 and 140 (FIG. 4). Rotation of adjusting knob 182 is transmitted via adjusting rod 194 to set screw 196 which displaces upper knife support bar 126 longitudinally relative to pusher block 112. The longitudinal displacement of knife support bar 126 results in pivotal movement of knife blade 130 about pivot shaft 134 to vary its angular orientation relative to jaw members 22 and 24. As a result, the vertical spacing between rollers 138 and 140 is varied in accordance with the vertical spacing between the jaw members.

After the tissue is clamped between the jaw members and the desired staple height is selected, the stapling instrument is fired by advancing pusher block 112 via actuator 114 to actuate the pusher bar and knife blade assembly 110. As pusher block 112 is advanced, staple pusher bars 120 are moved longitudinally along slots 56 provided in staple cartridge 50. The two wedge like cam surfaces 122 of staple pusher bars 120 move through slots 56 into engagement with sloped surfaces 124 of staple drivers 58 to sequentially drive the staples 55 from the cartridge and to form the staples into B-shaped configuration against anvil flanges 36. One cam surface 122 leads the other slightly to smooth and reduce the peak forces required to operate the stapling instrument. At the same time, knife blade 130 is advanced through central longitudinal slot 38 of anvil 40 and central longitudinal slot 52 of staple cartridge 50 to cut the tissue gripped between the jaw members after the staples are formed. As a result, the tissue is cut along a line located between the longitudinal staple rows. In addition, cylindrical rollers 138 and 140 serve as jaw support members which provide local support to the upper and lower jaw members as the pusher bar and knife blade assembly is advanced to staple and cut the tissue.

After pusher block 112 is fully advanced to drive all of the staples from cartridge 50, the pusher block is retracted to its start position. Thereafter, opposite sides 108 of latching spring 104 can be disengaged from pivot pin 74 to allow handle 26 to be unlatched. At this point, the cut and stapled tissue can be removed from the jaw members.

Figure 14:
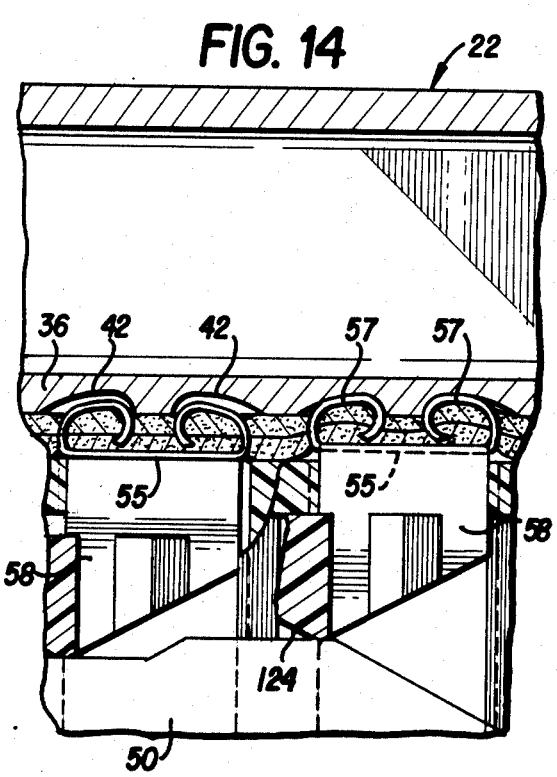
FIG. 14 illustrates the anastomotic stapling instrument during its tissue stapling operation with its jaw members adjusted to produce a small staple height.
Figure 15:
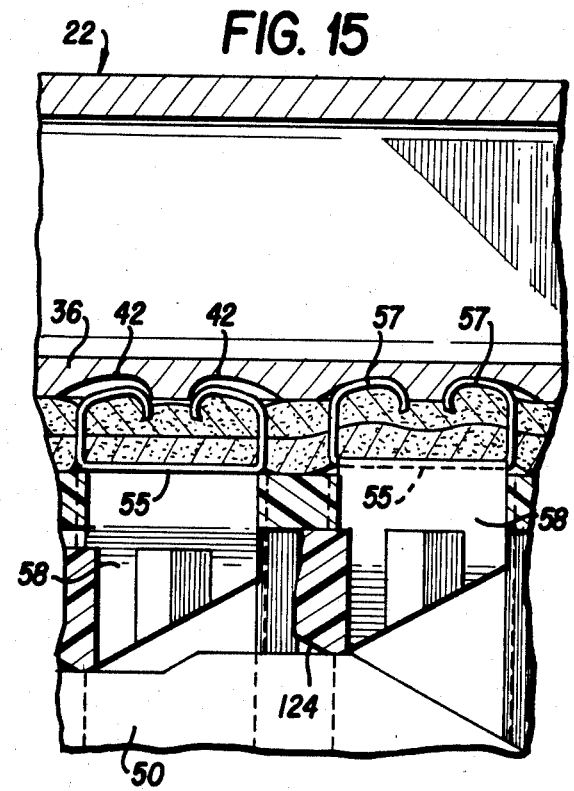
FIG. 15 illustrates the anastomotic stapling instrument during a tissue stapling operation with its jaw members adjusted to produce a large staple height.

The stapling instrument of the present invention advantageously allows adjustment of the height of the formed staples by varying the vertical spacing between the upper and lower jaw members. As shown in FIG. 14, with upper and lower jaw members 22 and 24 set to the minimum gap therebetweeen, the staple legs 57 of each staple 55 are driven into the tissue gripped between the jaw members and formed into B-shaped configuration to produce staples with the smallest staple height. As shown in FIG. 15, with upper and lower jaw members 22 and 24 set to the maximum gap therebetween, the staple legs 57 of each staple 55 are formed into B-shaped configuration to produce staples with the largest staple height. For example, the stapling instrument can be designed to achieve a minimum staple height of 1 mm and a maximum staple height of 3 mm. By actuation of its adjusting mechanism, any other desired intermediate staple height may be selected.

The invention in its broader aspects is not limited to the specific details shown and described, and modifications may be made in the structure of the linear anastomotic stapling instrument disclosed without departing from the principles of the present invention.

We claim:
1. A surgical stapling instrument, comprising:
   first and second cooperating elongate jaw members, one of said jaw members including staple carrying means adapted to receive a plurality of staples arranged in at least one row, and said other jaw member including anvil means adapted to form said staples,
   means for driving the staples from said staple carrying means into tissue gripped between said jaw members and forming the staples against said anvil means to produce at least one row of staples in the tissue, means for latching said jaw members together with the tissue located between said staple carring means and said anvil means, and adjusting means operable without unlatching said jaw members for varying the gap between said jaw members to adjust the spacing of said staple carrying means and said anvil means to select different staple heights to be produced when the staples are formed.

2. The surgical stapling instrument of claim 1, which includes:

support means adapted to maintain said jaw members in a spaced, parallel relationship as the gap therebetween is varied.

3. The surgical stapling instrument of claim 1, which includes:

first support means for pivotally connecting said elongate jaw members together at a first position therealong, said first support means being adjustable to vary the spacing between said jaw members at said first position, and second support means for adjustably connecting said elongate jaw members together at a second position therealong, said second support means being adjustable to vary the spacing between said jaw members at said second position.

4. The surgical stapling instrument of claim 3, wherein:

said adjusting means is adapted to simultaneously operate said first and second support means to adjust the gap between said jaw members.

5. A surgical stapling instrument, comprising:

first and second cooperating elongate jaw members, one of said jaw members including staple carrying means adapted to receive at least two laterally spaced longitudinal rows of staples, and said other jaw member including anvil means adapted to form said staples, a pusher bar and knife assembly slidable longitudinally relative to said elongate jaw members, said assembly including cam means for driving the staples from said staple carrying means into tissue gripped between said jaw members and forming the staples against said anvil means to produce a pair of laterally spaced staple rows in the tissue, and knife means for cutting the tissue gripped between said jaw members along a line between said staple rows.

means for latching said jaw members together with the tissue located between said staple carrying means and said anvil means, and adjusting means operable without unlatching said jaw members for varying the vertical spacing between said jaw members to adjust the spacing of said staple carrying means and said anvil means to select different closed staple heights to be produced when the staples are formed.

6. The surgical stapling instrument of claim 5, wherein said pusher bar and knife assembly includes:

a pair of jaw support members each cooperable with one of said elongate jaw members as said assembly is advanced to provide local support to said elongate jaw members, and means for adjusting the vertical spacing of said jaw support members as the vertical spacing between said elongate jaw members is varied.

7. The surgical stapling instrument of claim 6, wherein said pusher bar and knife assembly includes:

a knife blade oriented at an angle relative to said elongate jaw members, said jaw support members being carried by said knife blade, and said knife blade being adjustable to vary its angle of orientaton relative to said elongate jaw members and to vary the vertical spacing of said jaw support members.

8. The surgical stapling instrument of claim 5, which includes:

support means adapted to maintain said jaw members in a spaced, parallel arrangement as the vertical spacing therebetween is varied.

9. The surgical stapling instrument of claim 5, which includes:

pivot means for pivotally connecting the rearward ends of said elongate jaw members together, said pivot means being adjustable to vary the vertical spacing between said rearward ends of said jaw members, and gap setting means for connecting said elongate jaw members together at an intermediate position therealong, said gap setting means being adjustable to vary the vertical spacing between said jaw members.

10. The surgical stapling instrument of claim 8, wherein:

said adjusting means is adapted to simultaneously operate said pivot means and said gap setting means to vary the vertical spacing of said jaw members.

11. The surgical stapling instrument of claim 10, wherein:

one of said jaw members includes a slidable jaw section coupled to said pivot means and to said gap setting means and operable by said adjusting means for varying the vertical spacing between said jaw members as said slidable jaw section is displaced relative to said one jaw member.

12. A surgical stapling instrument comprising:

first and second cooperating elongate jaw members, one of said jaw members including a staple cartridge adapted to receive at least two laterally spaced longitudinal rows of staples and provided with staple drivers for driving the staples from said cartridge, and said other jaw member including an anvil adapted to form said staples, a pusher block slidably mounted for longitudinal movement along one of said jaw members and provided with a pair of staple pusher bars including cam surfaces engageable with said staple drivers for sequentially driving the staples from said cartridge and forming the staples against said anvil to produce a pair of laterally spaced staple rows in the tissue, a knife blade adjustably connected to said pusher block, said knife having a cutting edge oriented at an angle relative to said elongate jaw members, first and second jaw support members mounted on said knife blade for engaging said elongate jaw members as said pusher block is advanced to provide local support to said jaw members, and adjusting means for varying the vertical spacing between said jaw members and for adjusting the angular orientation of said knife blade to vary the vertical spacing of said jaw support members to select different closed staple heights to be produced when the staples are formed.

13. The surgical stapling instrument of claim 12, wherein said adjusting means includes:
   first and second knife support bars extending longitudinally from said pusher block, said knife blade being pivotally connected at first and second pivot points to said first and second knife support bars, respectively, and
   means for displacing one of said knife support bars longitudinally relative to said other knife support bar to vary the angular orientation of said knife blade and to adjust the vertical spacing of said jaw support members in accordance with the vertical spacing between said elongate jaw members.

14. The surgical stapling instrument of claim 13, wherein said displacing means includes:
   screw means rotatably mounted on said pusher block with one of said knife support bars being threadably engageable with said screw means to permit said one knife support bar to be advanced or retracted relative to said pusher block upon rotation of said screw means to adjust the angular orientation of said knife blade.

15. The surgical stapling instrument of claim 14, wherein said adjusting means includes:
   an adjusting knob rotatably mounted at the rearward end of one of said elongate jaw members, and
   means for slidably coupling said adjusting knob to said screw means to permit rotation of said adjusting knob to be transmitted to said screw means and to permit said pusher block and screw means to be advanced longitudinally relative to said adjusting knob.

16. The surgical stapling instrument of claim 15, wherein said coupling means includes:
   an adjusting rod extending longitudinally from said adjusting knob and mounted for rotation therewith, said adjusting rod being slidably connected and keyed to said screw means to transmit rotation of said adjusting knob to said screw means.

17. The surgical stapling instrument of claim 12, which includes:
   support means adapted to maintain said jaw members in a spaced, parallel arrangement as the vertical spacing therebetween is varied.

18. The surgical stapling instrument of claim 17, wherein said support means comprises:
   a rear pivot connection for pivotally connecting the rearward ends of said elongate jaw members together, said rear pivot connection being adjustable vertically to vary the spacing between the rearward ends of said jaw members,
   a pair of gap setting plates for connecting said elongate jaw members together at an intermediate position, said gap setting plates being adjustable vertically to vary the spacing between said jaw members, and
   said adjusting means is adapted to simultaneously adjust said rear pivot connection and said gap setting plates to maintain said jaw members in a spaced, parallel relationship as the vertical spacing therebetween is varied.

19. The surgical stapling instrument of claim 12, wherein:
   said anvil carrying jaw member includes an elongated passageway above said anvil for receiving said first jaw support means as said pusher block is advanced to allow said first jaw support means to travel along said anvil and provide local support to said first jaw member, and
   said staple cartridge carrying jaw member includes an elongated slot through which a portion of said knife blade protrudes, said second jaw support means being mounted on the protruding portion of said knife blade beneath said second jaw member to allow said second jaw support means to travel along and provide local support to said second jaw member.

20. The surgical stapling instrument of claim 19, wherein:
   said first and second jaw support means each comprise one or more rollers mounted at each of said first and second pivot points on said knife blade.

21. The surgical stapling instrument of claim 18, wherein:
   said staple cartridge carrying jaw member comprises an elongated, channel-shaped frame provided with a frame section slidably connected for longitudinal movement relative to said channel-shaped frame, said frame section being operatively coupled to said rear pivot connection and to said gap setting plates, and
   said adjusting mechanism is adapted to displace said slidable frame section longitudinally relative to said channel-shaped frame to adjust the height of said rear pivot connection and said gap setting plates to vary the vertical spacing between said jaw members.

* * * * *